(12) United States Patent
Murakami et al.

(10) Patent No.: US 8,045,171 B2
(45) Date of Patent: Oct. 25, 2011

(54) INSPECTION CHIP PRODUCING METHOD AND SPECIMEN DETECTING METHOD

(76) Inventors: Naoki Murakami, Ashigara-kami-gun (JP); Yuichi Tomaru, Ashigara-kami-gun (JP)

( * ) Notice: Subject to any disclaimer, the term of this patent is extended or adjusted under 35 U.S.C. 154(b) by 118 days.

(21) Appl. No.: 12/390,905

(22) Filed: Feb. 23, 2009

(65) Prior Publication Data

US 2009/0231586 A1    Sep. 17, 2009

(30) Foreign Application Priority Data

Mar. 14, 2008   (JP) .................................. 2008-065631

(51) Int. Cl.
G01N 21/55    (2006.01)

(52) U.S. Cl. ........................................ 356/445; 356/432
(58) Field of Classification Search .......... 356/445–448, 356/301, 432–440; 257/226, 444
See application file for complete search history.

(56) References Cited

U.S. PATENT DOCUMENTS

| 7,079,250 | B2 * | 7/2006 | Mukai ............................ 356/445 |
| 7,307,731 | B2 | 12/2007 | Naya |
| 2002/0150938 | A1 | 10/2002 | Kneipp et al. |
| 2005/0211566 | A1 | 9/2005 | Tomita et al. |
| 2006/0060472 | A1 | 3/2006 | Tomita et al. |
| 2006/0183236 | A1 | 8/2006 | Berlin et al. |
| 2007/0263221 | A1 | 11/2007 | Naya et al. |
| 2009/0098344 | A1 * | 4/2009 | Tomaru ......................... 428/172 |
| 2009/0248367 | A1 * | 10/2009 | Naya et al. .................... 702/194 |
| 2009/0273780 | A1 * | 11/2009 | Tomaru et al. ................. 356/301 |
| 2010/0294926 | A1 * | 11/2010 | Murakami .................... 250/282 |

FOREIGN PATENT DOCUMENTS

| EP | 1 541 994 A1 | 6/2005 |
| EP | 2 053 383 A1 | 4/2009 |
| JP | 2005-144569 A | 6/2005 |
| JP | 2005-195440 A | 7/2005 |
| JP | 2007-240361 A | 9/2007 |
| WO | 2008/010442 A1 | 1/2008 |

OTHER PUBLICATIONS

EP Communication, dated Jun. 19, 2009, issued in corresponding EP Application No. 09002752.5, 9 pages.

Kneipp et al., "Detection and identification of a single DNA base molecule using surface-enhanced Raman scattering (SERS)," Physical Review E. Statistical Physics, Plasmas, Fluids, and Related Interdisciplinary Topics, vol. 57, No. 6, Jun. 1, 1998, pp. R6281-RR6284, XP-002106894.

* cited by examiner

Primary Examiner — Hoa Pham
(74) Attorney, Agent, or Firm — Sughrue Mion, PLLC

(57) ABSTRACT

A method of producing an inspection chip includes a microstructure producing step of producing a microstructure where metallic portions having dimensions permitting excitation of surface plasmons are formed and distributed on one surface of a substrate, a specimen attaching step of attaching a specimen to the surfaces of the metallic portions of the microstructure, and a metallic particle attaching step of attaching metallic particles having dimensions permitting excitation of surface plasmons to the metallic portions and the specimen, wherein the specimen is attached to the metallic portions to which no substance capable of specifically binding to the specimen is secured in the specimen attaching step, and/or the metallic particles to which no substance capable of specifically binding to the specimen is secured are attached to the specimen in the metallic particle attaching step.

18 Claims, 6 Drawing Sheets

INSPECTION CHIP PRODUCING METHOD AND SPECIMEN DETECTING METHOD

The entire contents of documents cited in this specification are incorporated herein by reference.

BACKGROUND OF THE INVENTION

The invention relates to a method of producing an inspection chip used for a specimen detection device that detects a specimen using localized plasmons and a specimen detecting method of detecting a specimen using localized plasmon.

Among known detection devices for detecting a minute specimen is one using an enhanced electric field created by localized plasmons or an enhanced electric field further intensified by localized plasmon resonance, which is a phenomenon where resonance is produced by coupling between localized plasmons and light.

In a detection device of this type, a specimen is placed on a substrate on a surface of which a number of metallic portions capable of exciting localized plasmons are disposed, with Raman scattered light of the specimen intensified by an enhanced electric field that is generated by localized plasmons. Since Raman scattered light displays a spectrum proper to each specimen under examination, the specimen can be identified or existence of a specific specimen can be determined by detecting Raman scattered light of the specimen.

Substrates that generate an enhanced electric field intensified by localized plasmon resonance include, for example, ones having configurations described in JP 2005-144569 A and JP 2007-240361 A.

JP 2005-144569 A describes a substrate on which particles each coated with a thin metallic film are disposed with a high density. To be more specific, JP 2005-144569 A describes a substrate having a two-dimensional array structure formed by reducing dielectric or semiconductor particles densely arranged on the substrate through anisotropic dry etching process and attaching a metal or a semiconductor onto the particles in a hemispherical form by vapor deposition or sputtering to keep the metallic parts of adjacent particles spaced at a given controlled distance.

JP 2007-240361 A describes a substrate having a number of minute projections formed thereon. The projections have a metallic layer disposed on the surface thereof; the metallic layer has a dielectric layer formed on the surface thereof, and the dielectric layer has secured to the surface thereof specific binding members capable of specifically binding to a substance to be measured that is contained in a test sample to form a specific binding substance.

JP 2005-195440 A describes a specimen detecting method using a microstructure comprising a substrate and first metallic particles. The substrate has micropores formed and distributed on one surface thereof. The first metallic particles each have dimensions permitting excitation of localized plasmon resonance and are disposed in the micropores of the substrate so that the head portions of the first metallic particles project above the surface of the substrate. The microstructure is placed in a solution with a substance capable of specifically binding to the specimen secured to the head portions of the first metallic particles. The solution contains dispersed therein second metallic particles having dimensions permitting excitation of localized plasmon resonance, with a substance capable of specifically binding to the specimen secured to the second metallic particles. The surface of the microstructure from which the head portions of the first metallic particles project is irradiated by light to measure the intensity of light component reflected or transmitted at said surface, thereby detecting the specimen contained in the solution based upon the measured intensity of the light.

According to the method described in JP 2005-195440 A, the specimen binds to the second metallic particles to which a substance capable of specifically binding to the specimen is secured whereas the specimen also binds to the first metallic particles to the head portions of which a substance capable of specifically binding to the specimen is secured, so that the change in plasmon resonance wavelength that varies greatly when the first metallic particles and the second metallic particles approach is detected to achieve detection of the specimen.

In the detection devices using the substrates described in JP 2005-144569 A and JP 2007-240361 A, the metallic particles or metallic projections having dimensions permitting excitation of localized plasmon resonance are allowed to adsorb specimen to detect, for example, the variation in an enhanced electric field, fluorescent light from the specimen excited by the enhanced electric field, and Raman scattered light thereby to achieve detection of the specimen.

According to such a method, however, a great enhancement cannot be achieved because only an enhanced electric field created around metallic particles that lie below the specimen can be used.

Although, according to the method described in JP 2007-240361 A, the efficiency with which the specimen binds to the metallic film may be increased by securing a substance capable of specifically adsorbing the specimen to the surface of the metallic film, a great enhancement cannot be achieved because, also in this case, only an enhanced electric field created around metallic particles that lie below the specimen can be used.

Furthermore, the need to select for each specimen a specific adsorbing substance for attachment to the metallic particles adds to the cumbersome procedure and limits the specimen to which the detection device can be used.

The method proposed in JP 2005-195440 A, which detects the variation of a plasmon resonance wavelength, requires the specific adsorption to be performed twice. Accordingly, two or more molecules of a specific adsorbing substance (referred to as "antibody" below) needs to be bound to the specimen. Thus, where the specimen is a substance having a small molecular mass, two molecules of an antibody cannot be adsorbed onto the specimen, making the detection of the specimen impossible.

Furthermore, because the method described in JP 2005-195440 A achieves detection of the variation in plasmon resonance wavelength caused as the first metallic particles and the second metallic particles come close to each other through the intermediary of the specimen, it is essential that the first metallic particles and the second metallic particles approach each other only through the intermediary of the specimen.

SUMMARY OF THE INVENTION

Thus, an object of the invention is to provide a detection chip producing method whereby the above problems associated with the prior art are eliminated and a specimen can be detected with a high sensitivity. Another object of the invention is to provide a specimen detecting method whereby a specimen can be detected with ease and with a high sensitivity.

A method of producing an inspection chip according to the invention comprising: a microstructure producing step of producing a microstructure where metallic portions having dimensions permitting excitation of localized plasmons are formed and distributed on one surface of a substrate; a specimen attaching step of attaching a specimen to surfaces of the metallic portions of the microstructure; and a metallic particle attaching step of attaching metallic particles having dimensions permitting excitation of surface plasmons to the specimen;

wherein the specimen is attached to the metallic portions to which no substance capable of specifically binding to the specimen is secured in the specimen attaching step, and/or the metallic particles to which no substance capable of specifically binding to the specimen is secured are attached to the specimen in the metallic particle attaching step.

A method of detecting a specimen according to the invention comprising: an inspection chip producing step of producing an inspection chip using such method of producing an inspection chip; a measuring step of irradiating the substrate with light to measure light transmitted through or reflected by a plane in which the metallic portions are formed; and a detecting step of detecting the specimen based upon intensity of light measured in the measuring step.

BRIEF DESCRIPTION OF THE DRAWINGS

The invention will be better understood by reference to the following description taken in conjunction with the accompanying drawings in which.

DESCRIPTION OF THE PREFERRED EMBODIMENTS

Now, the inspection chip producing method and the specimen detecting method according to the invention will be described in detail based upon embodiments illustrated in the attached drawings.

Figure 1:
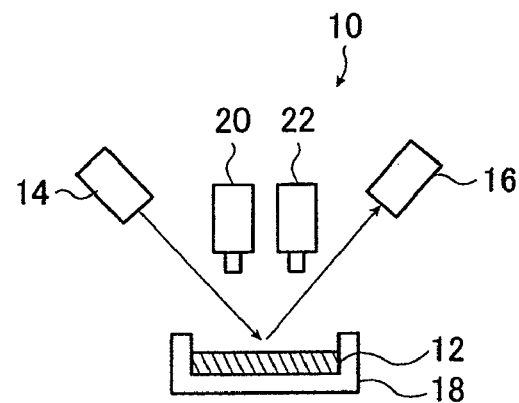
FIG. 1 is a block diagram illustrating a schematic configuration of an embodiment of the specimen detecting device using the specimen detecting method of the invention.
Figure 2:
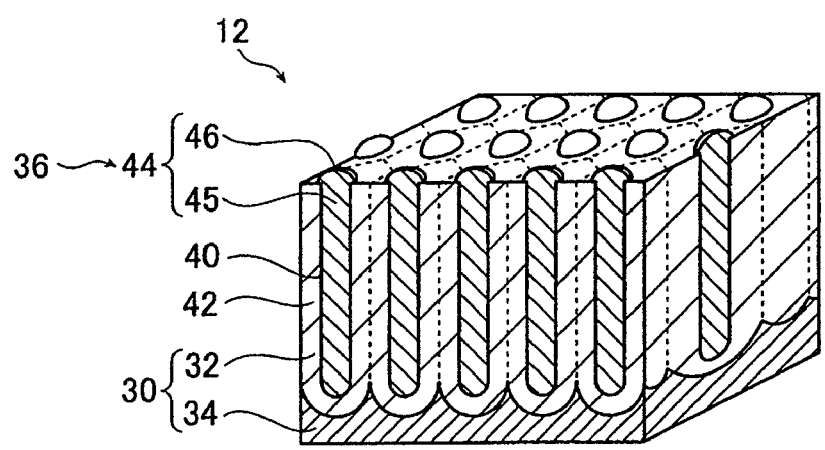
FIG. 2 is a perspective view of a schematic configuration of an embodiment of a microstructure used for the specimen detecting device illustrated in FIG. 1.

FIG. 1 is a front view illustrating a schematic configuration of a specimen detecting device 10 using the inspection chip producing method and the specimen detecting method according to the invention; FIG. 2 is a perspective view of a schematic configuration of a microstructure 12 used for the specimen detecting device 10 illustrated in FIG. 1.

As illustrated in FIG. 1, the specimen detecting device 10 comprises the microstructure 12, light radiating means 14 for irradiating the microstructure 12 with light, light detection means 16 for detecting reflected light reflected by the microstructure 12, chip support means 18 for supporting the microstructure 12, specimen dropping means 20 for dropping a liquid containing the specimen onto the microstructure 12, and metallic particle dropping means 22 for dropping a liquid containing metallic particles onto the microstructure 12.

The specimen detecting device 10 further comprises various other members required of the specimen detecting device 10 such as a housing covering the microstructure 12, the light radiating means 14, the light detection means 16, and other components, optical members such as a filter for eliminating stray light occurring inside the specimen detecting device 10, and a control unit for controlling the operations of the specimen detecting device 10, though not shown.

As illustrated in FIG. 2, the microstructure 12 comprises a substrate 30 including a dielectric base 32 and an electric conductor 34 disposed on one surface of the dielectric base 32 and metallic members 36 disposed on the side of the dielectric base 32 opposite from the electric conductor 34.

The substrate 30 comprises the dielectric base 32 formed of a metallic oxide ($Al_2O_3$) and the electric conductor 34 disposed on the one surface of the dielectric base 32 and formed of a non-anodized metal (Al). The dielectric base 32 and the electric conductor 34 are formed integrally.

The dielectric base 32 has micropores 40 each having the shape of a substantially straight tubing that extends from the surface opposite from the electric conductor 34 toward the surface closer to the electric conductor 34.

Each micropore 40 is formed through the surface of the dielectric base 32 so as to have an opening at one end thereof opposite from the electric conductor 34, with the other end closer to the electric conductor 34 closing short of the opposite surface of the dielectric base 32. In other words, the micropores 40 do not reach the electric conductor 34. The micropores 40 each have a diameter smaller than the wavelength of the excitation light and are arranged regularly at a pitch smaller than the wavelength of the excitation light.

When the excitation light used is a visible light, the micropores 40 are preferably arranged at a pitch of 200 nm or less.

The metallic members 36 are formed of rods 44 each having a filler portion 45 filling the inside of each micropore 40 of the dielectric base 32 and a metallic portion or, a projection 46 (bulge) in the illustrated example, which has an outer diameter greater than that of the filler portion 45 and has dimensions permitting excitation of localized plasmons. Although, in the illustrated example, the metallic portions distributed on the surface of the dielectric base 32 of the microstructure 12 used in the invention are each formed of a projection 46 providing a bulge, the invention is not limited to such a configuration. The metallic portions may have any shape, provided that they have dimensions permitting excitation of localized plasmons. The material for forming the metallic members 36 may be selected from various metals capable of exciting localized plasmons and include, for example, Au, Ag, Cu, Al, Pt, Ni, Ti, and an alloyed metal thereof. Further, the metallic members 36 may also contain two or more of these metals. To obtain a further enhanced field effect, the metallic members 36 are more preferably formed using Au or Ag.

The microstructure 12 has a configuration as described above such that the surface on which the projections 46 of the rods 44 of the metallic members 36 are arranged provide a surface on which a substance to be analyzed is placed, that is, a detection surface.

The light radiating means 14 comprises a light source such as a laser light source and a light guiding system for guiding light emitted by the light source. The light radiating means 14 emits light having a specific wavelength (excitation light) and irradiates the detection surface of the microstructure 12 with the excitation light.

The light detection means 16 may be, for example, a spectral detector and is disposed in a position allowing the light detection means 16 to receive scattered light occurring at the detection surface of the microstructure 12 as the light radiating means 14 radiates light.

The light detection means 16 disperses the scattered light occurring at the detection surface of the microstructure 12 and detects Raman spectra of Raman scattered light.

The chip support means 18 is a seating or the like and holds the microstructure 12 in a given position by supporting the microstructure 12 from the side thereof bearing the electric conductor 34. The chip support means 18 comprises an enclosure for covering the outer periphery of the lateral sides of the microstructure 12 to prevent a liquid from spilling out from the surface of the microstructure 12 when the liquid is dropped onto the microstructure 12.

The specimen dropping means 20 comprises a reservoir for storing a liquid containing a specimen and a dropping mechanism for dropping the liquid containing the specimen stored in the reservoir onto the microstructure 12. The specimen dropping means 20 is disposed opposite the detection surface of the microstructure 12. The dropping mechanism may be a dropper or the like.

The specimen dropping means 20 drops a given amount of liquid containing the specimen onto the detection surface of the microstructure 12.

The solvent for dispersing the specimen may be selected from various solvents such as water and ethanol. In this embodiment, a volatile solvent is preferably used and specifically ethanol. To detect a specimen that, for example, is contained in a liquid sample, the liquid sample itself may be dropped.

The metallic particle dropping means 22 comprises a reservoir for storing a liquid containing metallic particles and a dropping mechanism for dropping the liquid containing metallic particles stored in the reservoir onto the microstructure 12. The metallic particle dropping means 22 is disposed opposite the detection surface of the microstructure 12. The metallic particle dropping means 22 may for example be a dropper like the specimen dropping means 20.

The metallic particle dropping means 20 drops a given amount of liquid containing the metallic particles onto the detection surface of the microstructure 12.

The metallic particles herein are particles having dimensions permitting excitation of localized plasmons.

The material for forming the metallic particles may be any of the metals described earlier for forming the metallic members of the microstructure. Accordingly, various metals permitting excitation of localized plasmons may be used such as, for example, Au, Ag, Cu, Al, Pt, Ni, Ti, and an alloyed metal thereof. The metallic members 36 may contain two or more of these metals. To obtain a further enhanced field effect, the metallic members 36 are more preferably formed using Au or Ag. The metal or metals used to form the metallic particles may be the same as or different from the metal or metals used to form the metallic members 36.

The solvent for dispersing the metallic particles may be any of various solvents such as water, ethanol, and aqueous solutions containing a substance selected from a variety of substances, such as an aqueous solution of citric acid. In this embodiment, a volatile solvent is preferably used, specifically ethanol.

The specimen detecting device 10 has a basic configuration as described above.

Now, the inspection chip producing method and the specimen detecting method according to the invention will be described in greater detail by describing the operations of the specimen detecting device 10.

Figure 3A:
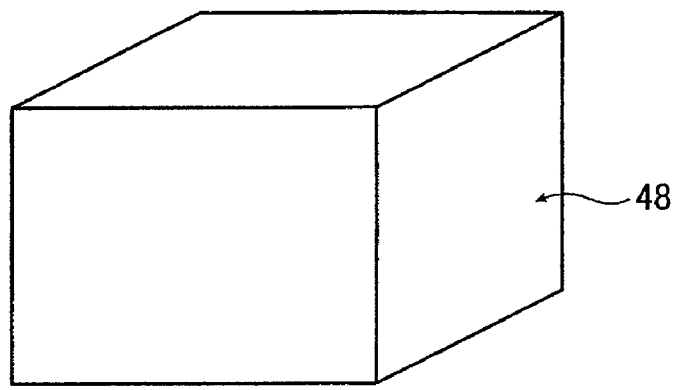
FIGS. 3A to 3C illustrate a process for producing a microstructure.
Figure 3B:
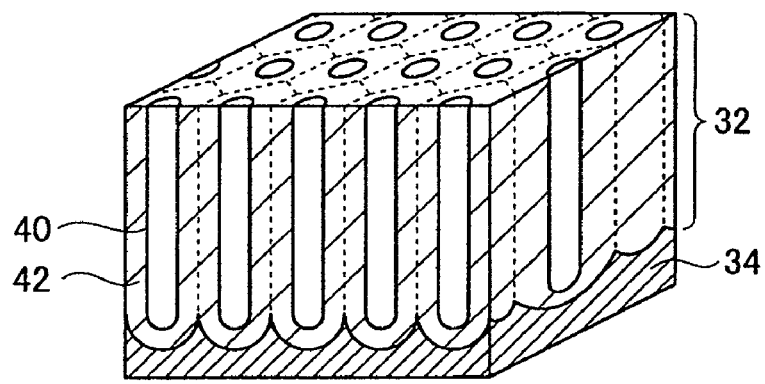
Figure 3C:
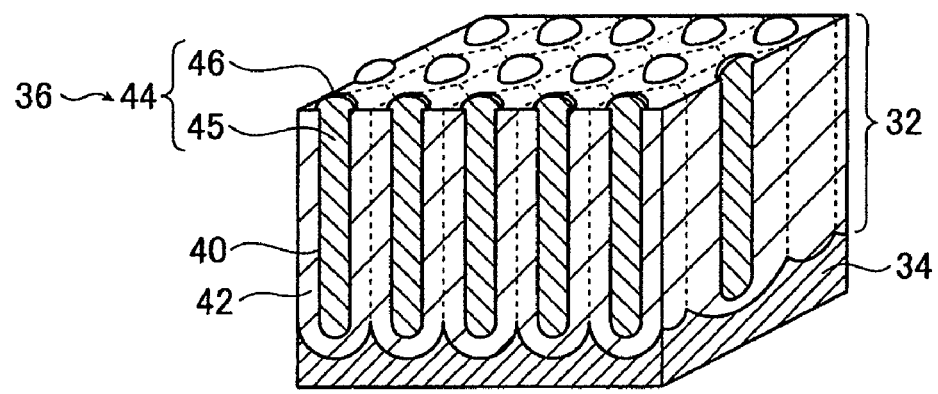
Figure 4A:
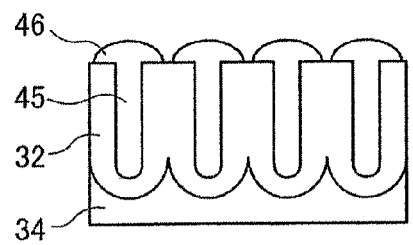
FIGS. 4A to 4C illustrate a process for producing an inspection chip of the invention.
Figure 4B:
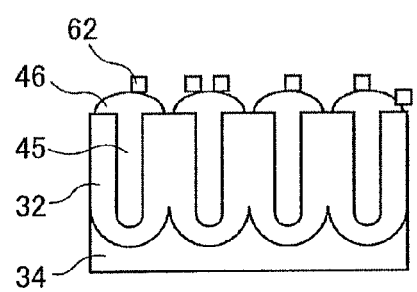
Figure 4C:
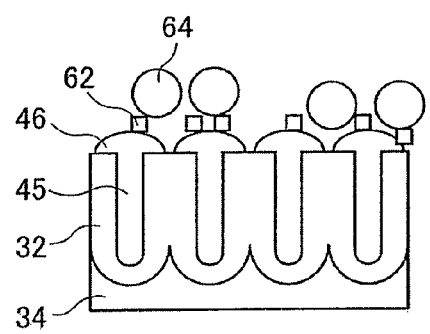

FIGS. 3A to 3C illustrate an example of the process for producing the microstructure 12; FIGS. 4A to 4C illustrate a process for producing an inspection chip of the invention.

First, the method of producing the microstructure 12 used for the specimen detecting device 10 will be described.

First, a metallic body 48 to be anodized having the shape of a rectangular solid as illustrated in FIG. 3A is anodized. Specifically, the metallic body 48 to be anodized is submerged in an electrolytic solution as an anode together with a cathode, whereupon an electric voltage is applied between the anode and the cathode to achieve anodization.

The cathode may be formed, for example, of carbon or aluminum. The electrolytic solution is not limited specifically; preferably used is an acid electrolytic solution containing at least one of sulfuric acid, phosphoric acid, chromic acid, oxalic acid, sulfamic acid, benzenesulfonic acid and amidosulfonic acid.

Although the metallic body 48 to be anodized has the shape of a rectangular solid in this embodiment, the shape is not limited thereto and may vary. Further, one may use a configuration comprising a support member on which, for example, a layer of the metallic body 48 to be anodized is formed.

Anodization of the metallic body 48 causes oxidation to take place as illustrated in FIG. 3B from the surface of the metallic body 48 in a direction substantially vertical to that surface, producing a metallic oxide ($Al_2O_3$), which is used as the dielectric base 32. The metallic oxide produced by anodization or the dielectric base 32 has a structure wherein numerous minute columns 42 each having a substantially hexagonal shape in planar view are arranged leaving no space between them.

The minute columns 42 each have a round bottom end and a micropore 40 positioned substantially at its center and extending straight from the top surface in the depth direction, i.e., in the direction of the axis of each minute column 42. For the structure of a metallic oxide produced by anodization, reference may be had, for example, to "Production of Mesoporous Alumina using Anodizing Method and Applications Thereof as Functional Material" by Hideki Masuda, page 34, Zairyo Gijutsu (Material Technology), Vol. 15, No. 10, 1997.

An example of preferred anodization conditions for producing a metal oxide having a regularly arrayed structure includes an electrolytic solution having a concentration of 0.5 M, a liquid temperature in the range of 14° C. to 16° C., and an applied electric voltage of 40 V to 40 V+/−0.5 V among other conditions when using oxalic acid as an electrolytic solution. The micropores 40 produced under these conditions each have, for example, a diameter of about 30 nm and are arranged at a pitch of about 100 nm.

Next, the micropores 40 of the dielectric base 32 are electroplated to form the rods 44 each having the filler portion 45 and the projection 46 as illustrated in FIG. 3C.

In the electroplating, the electric conductor 34 acts as an electrode, causing a metal to be deposited preferentially from the bottoms of the micropores 40 where the electric field is stronger. Continuous electroplating causes the micropores 40 to be filled with a metal, forming the filler portions 45 of the rods 44. Electroplating further continued after the formation of the filler portions 45 causes the metal to overflow from the micropores 40. However, the electric field near the micropores 40 is so strong that the metal continues to be deposited around each micropore 40 until the metal is deposited above the filler portions 45 so as to project from the surface of the dielectric base 32, thus forming the projections 46 having a diameter greater than that of the filler portions 45.

This is how the microstructure 12 is produced.

Next, the microstructure 12 thus produced is placed upon the chip support means 18 and held in a given position (see FIG. 4A).

Then, a liquid containing a specimen 62 is dropped onto the detection surface of the microstructure 12. Thereafter, the liquid on the detection surface (the solvent) is dried.

Drying the liquid causes the specimen 62 to attach to the surface of the projections 46 of the metallic members 36 of the microstructure 12 as illustrated in FIG. 4B.

Next, a liquid containing metallic particles 64 is dropped from the metallic particle dropping means 22 onto the detection surface of the microstructure 12. Then, the liquid on the detection surface is dried.

Drying the liquid causes the metallic particles 64 to be attached around the projections 46 to which the specimen 62 has been attached as illustrated in FIG. 4C.

Thus produced is an inspection chip where the specimen 62, which is an object of measurement, and the metallic particles 64 are placed in layers upon the detection surface of the microstructure 12.

Next, light is emitted from the light emitting means 14 to irradiate the detection surface (i.e., the detection surface of the microstructure 12 or the surface to which the specimen 62 is attached).

When irradiated by the light emitted from the light emitting means 14, the detection surface of the inspection chip produces localized plasmons on the surfaces of the projections 46 of the metallic members 36 and the surfaces of the metallic particles 64 to generate electric fields.

In hot spots or regions where the metallic particles and the projections generating localized plasmons come as close as less than several tens of nanometers to each other, extremely enhanced electric fields are generated. In the inspection chip, hot spots are formed between metallic particles, between projections, and between metallic particles and projections that are as close to each other as mentioned above.

Further, the inspection chip effectively generates localized plasmon resonance that further enhances the electric field at the surfaces of the projections 46 of the metallic members 36 and the surfaces of the metallic particles 64. The localized plasmon resonance is a phenomenon where the electric field is further enhanced as free electrons of a metal in a localized collective motion caused by localized plasmons oscillate in resonance with the optical electric fields. In the irregular configuration of the inspection chip formed by the projections 46 (bulges) and/or the metallic particles 64, free electrons of the projections 46 (bulges) and/or the metallic particles 64 oscillate in resonance with the optical electric fields in regions where the wavelength of an incident light agrees with the dimensions of the irregular configuration, and the incident light is efficiently changed into the electric fields, to further enhance the electric fields around the projections 46 and/or the metallic particles 64.

Thus, the inspection chip achieves a high field enhancement effect at the detection surface, creating an enhanced electric field. Although it is preferable to design and adjust the wavelength of the excitation light and the dimensions of the projections and the metallic particles of the inspection chip in such a manner as to cause localized plasmon resonance at the projections and the metallic particles in order to achieve a further enhanced electric field, localized plasmons need only be generated at least at the projections and the metallic particles.

The specimen on the detection surface generates Raman scattered light as an excitation light having a specific wavelength hits the specimen. Raman scattered light generated by the specimen is intensified by the electric field generated by the localized plasmon. That is, Raman scattered light is intensified by Raman enhancement effect. The spectrum of Raman scattered light varies with the kind of a sample measured.

The light detection means 16 detects scattered light on the detection surface of the microstructure 12 and detects the kind and/or the amount of the specimen from the results of the detection.

This is how the specimen detecting device 10 detects the specimen.

Thus, the specimen detecting device 10 is capable of trapping the specimen between the projections and the metallic particles by first attaching the specimen to the detection surface of the microstructure on which the metallic projections are formed and then attaching the metallic particles (or allowing the metallic particles to settle in proximity). In other words, attaching the metallic particles (or placing them in close proximity) ensures that in a state where the specimen is attached onto the projections of the microstructure, the metallic particles can be attached to (or placed in close proximity to) the side of the specimen that is not in contact with the projections. Thus, a plurality of bodies that generate localized plasmons can be placed around one piece of the specimen to increase the area where the specimen is attached to or lies close to metallic particles or projections with the result that a greater number of enhanced electric fields (to be precise, enhanced electric fields created by localized plasmons) can be generated around the specimen.

Further, the specimen can be located in hot spots formed between the projections and the metallic particles by attaching the specimen to the projections and attaching the metallic particles to the specimen or placing the metallic particles close to the specimen, thereby creating further enhanced electric fields around the specimen.

Thus, a greater number of further enhanced electric fields can be created around the specimen, and Raman scattered light produced from the specimen can be further intensified (i.e., Raman enhancement effect can be further increased), whereby the specimen can be detected with an increased level of sensitivity.

Further, the specimen can be detected without specifically binding the specimen to the projections and/or the metallic particles because the specimen can be identified by detecting the Raman scattered light of the specimen attached to the projections. This permits detection of a specimen without the need to select a substance that specifically binds to a specimen (referred to as "specific binding substance" below) for the projections and/or the metallic particles with respect to each specimen and secure the selected specific binding substance to the projections and/or the metallic particles in order to bind the specimen to the projections and/or the metallic particles.

Further, since no specific binding substance need be used, various specimens contained in a sample can be identified from detected spectral distributions in a single inspection.

Still further, since the specimen need not be bound to any specific binding substance, detection is possible even when the specimen is a substance too small to permit specific binding.

Now, the present invention will be described in greater detail by referring to specific examples. In an example now to be described, the liquid containing a specimen was an R6G ethanol solution produced by dissolving R6G, a specimen, in ethanol, a solvent, to a concentration of 100 μM. The liquid containing metallic particles used in the example was a colloidal gold solution provided by Tanaka Kikinzoku Kogyo K.K. containing gold nanoparticles each having a particle diameter of 60 nm. The microstructure used in the example had metallic members made of gold (i.e., projections made of gold) and measured 1 cm×1 cm.

First, 10 μl of R6G ethanol solution was dropped onto the detection surface of the microstructure and dried. Then, 10 μl of colloidal gold solution was dropped onto the detection surface of the microstructure and dried.

An inspection chip thus produced was irradiated by light emitted from the light radiating means to detect the spectrum of the scattered light occurring at the detection surface with the light detection means.

The excitation light emitted from the light radiating means had an excitation wavelength of 785 nm and a laser power of 2 mW at the point where it focuses.

The light detection means measured light emitted from the detection surface for 10 seconds to obtain an accumulated value. The measurement was repeated twice, and an average thereof was used as a detected spectrum.

For comparison, the same inspection chip as the above inspection chip was produced except that the metallic particles were not dropped onto its detection surface (i.e., only the specimen was disposed on the detection surface).

To provide a comparative example, measurement was also made of the spectrum of scattered light occurring at the detection surface of the inspection chip onto which no metallic particles were dropped.

Figure 5A:
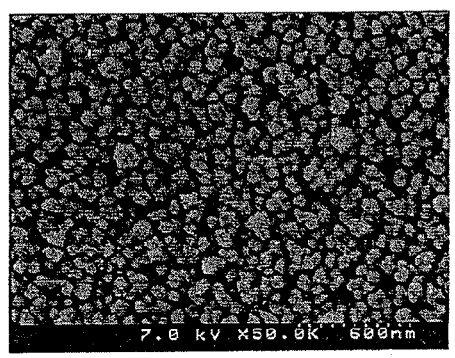
FIGS. 5A and 5B are each top plan views of a microstructure.
Figure 5B:
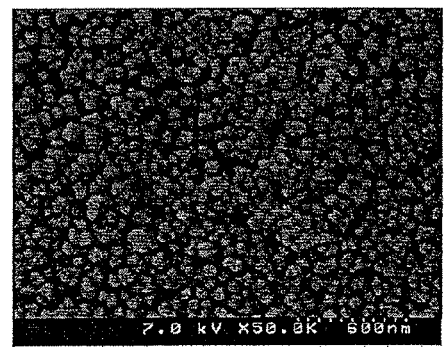

FIGS. 5A and 5B illustrate detection surfaces as observed before and after the metallic particles were dropped onto the detection surface. FIG. 5A is a top plan view of the detection surface before the metallic particles were dropped; FIG. 5B is a top plan view of the detection surface after the metallic particles were dropped.

Metallic particles dropped onto the detection surface where, as can be seen in FIG. 5A, projections (numerous white areas in FIG. 5A) are formed change the detection surface into the one illustrated in FIG. 5B where numerous projections and metallic films (numerous white areas in FIG. 5B) are formed and disposed.

Thus, the metallic components on the detection surface increase when the metallic particles are dropped onto the detection surface.

Figure 6:
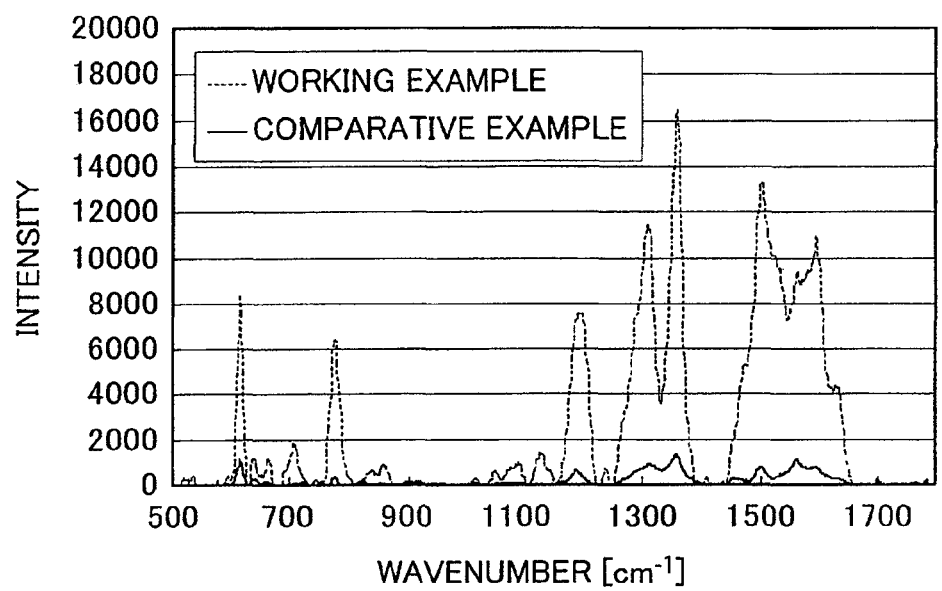
FIG. 6 is a graph illustrating a spectral distribution of light detected by light detection means.

FIG. 6 illustrates obtained measurements of spectra of the working example of the invention and the comparative example. FIG. 6 is a graph illustrating spectral distributions of the light detected by the light detection means. The horizontal axis indicates wavenumber [cm$^{-1}$] and the vertical axis indicates intensity. The dotted line represents a measurement of the spectrum obtained from the working example and a solid line represents a measurement of the spectrum obtained from the comparative example.

FIG. 6 shows that Raman scattered light can be further intensified when the metallic particles are dropped after the specimen is dropped onto the detection surface as compared with the case where only the specimen is dropped onto the detection surface.

Table 1 below shows detection results (specifically, measured intensities) at wavenumbers of 1360 cm$^{-1}$ and 1500 cm$^{-1}$ corresponding to Raman scattered light wavelengths specific to R6G placed as specimen and a calculated intensity ratio between the comparative example and the working example.

TABLE 1

|  | Measured intensity | | Intensity ratio between working example and comparative example | |
| --- | --- | --- | --- | --- |
|  | 1360 cm$^{-1}$ | 1500 cm$^{-1}$ | 1360 cm$^{-1}$ | 1500 cm$^{-1}$ |
| Working example | 16456 | 13289 | 12.55895596 | 17.20637551 |
| Comparative example | 1310.3 | 772.33 | 1 | 1 |

It appears from Table 1 that Raman scattered light emitted from R6G can be further intensified when the metallic particles are provided and detection can be made with an increased intensity as compared with the case where the metallic particles are not provided.

Specifically, detection can be made with an intensity that is about 12 times greater at 1360 cm$^{-1}$ and about 17 times greater at 1500 cm$^{-1}$ than when the metallic particles are not provided as shown in Table 1. Thus, detection can be made with a sensitivity that is increased by 1 digit.

The effects produced by the invention are obvious from the foregoing description.

Since the microstructure 12 according to the above embodiment is produced using anodization, it is easy to produce the microstructure 12 where the micropores 40 of the dielectric base 32 and the projections 46 of the metallic members 36 are arranged substantially regularly. Alternatively, the micropores may be arranged randomly.

Although only Al is cited as a major component of the metallic body 48 to be anodized that is used to produce the dielectric base 32 in the above embodiment, any metal may be used, provided that it is anodizable and that the resulting metallic oxide is translucent. Other metals than Al that may be used include Ti, Ta, Hf, Zr, Si, In, and Zn. The metallic body 48 to be anodized may contain two or more kinds of anodizable metals.

The shape of the microstructure is not limited to that of the microstructure 12; the microstructure may have various other shapes, provided that the microstructure has projections formed on the substrate thereof each having dimensions permitting excitation of localized plasmon.

Figure 7A:
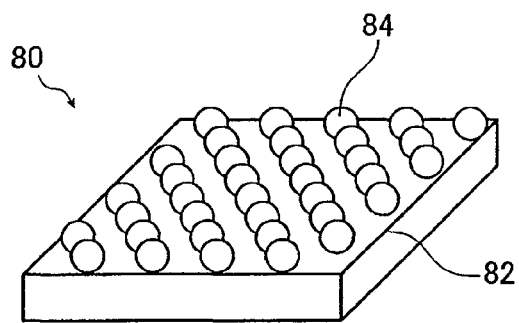
FIG. 7A is a perspective view illustrating a schematic configuration of another example of microstructure.
Figure 7B:
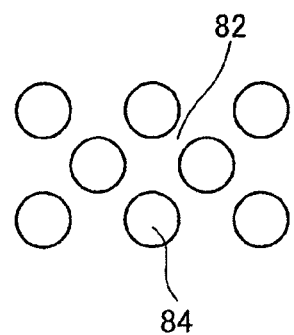
FIG. 7B is a partial top plan view of FIG. 7A.

FIG. 7A is a perspective view illustrating a schematic configuration of another example of the microstructure; FIG. 7B is a top plan view of FIG. 7A.

A microstructure 80 illustrated in FIGS. 7A and 7B comprises a substrate 82 and numerous metallic particles 84 disposed on the substrate 82.

The substrate 82 is a base material in the form of a plate. The substrate 82 may be formed of a material capable of supporting the metallic particles 84 in an electrically insulated state. The material thereof is exemplified by silicon, glass, yttrium-stabilized zirconia (YSZ), sapphire, and silicon carbide.

The numerous metallic particles 84 are each of dimensions permitting excitation of localized plasmons and held in position such that they are spread on one surface of the substrate 82.

The metallic particles 84 may be formed of any of the metals cited above for the metallic members 36. Further, the metallic particles 84 may be formed of the same metal as or a different metal from the one used to form the metallic particles 64 described earlier. The shape of the metallic particles is not limited specifically; it may be a sphere or a rectangular solid.

The microstructure 80 having such a configuration also generates localized plasmons around the metallic particles and creates an enhanced electric field when the detection surface on which the metallic particles are disposed is irradiated by the excitation light.

Now, the method of producing the inspection chip using the microstructure 80 will be described referring to FIG. 8.

Figure 8A:
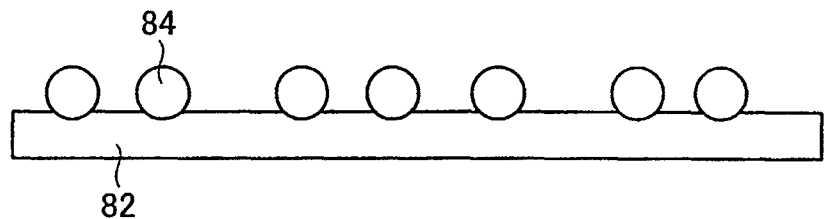
FIGS. 8A to 8C illustrate another example of a process for producing an inspection chip using the microstructure of FIG. 7.
Figure 8B:
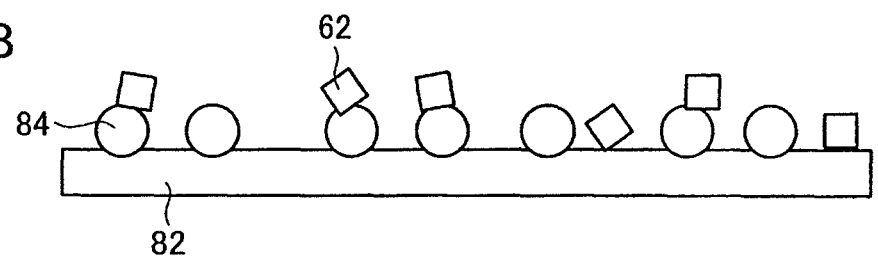
Figure 8C:
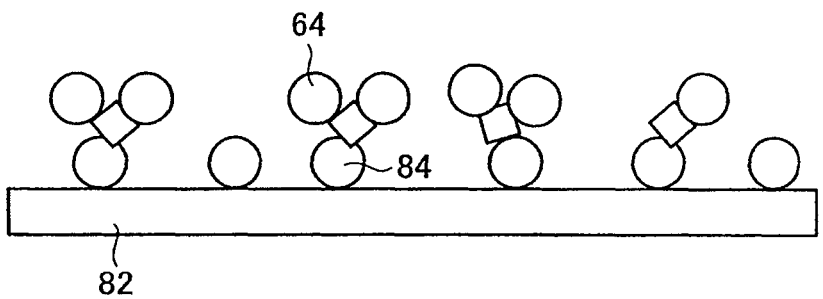

FIGS. 8A to 8C illustrate a process for producing the inspection chip using the microstructure 80.

First, numerous metallic particles 84 are secured to the substrate 82 to produce the microstructure 80 as illustrated in FIG. 8A.

The metallic particles 84 may be secured to the substrate 82 by any of various methods including but not limited to a method using silane coupling, a method whereby citric acid is replaced by CTBA, followed by spontaneous evaporation, a method whereby a solution containing the metallic particles 84 is applied onto the substrate 82 and the solvent is allowed to evaporate spontaneously, a method whereby a thin film is formed on the substrate 82 and then removed using lithography, etching, sputtering, or like process, to leave only the parts thereof that will be metallic particles, a method whereby metallic particles are vapor-deposited on the substrate 82 (vapor deposition is terminated immediately after vapor deposition onto the substrate 82 is started in order to achieve partial vapor deposition on the substrate 82), and a method whereby a metallic film is vapor-deposited on the substrate 82 and then annealed for concentration thereof to produce the metallic particles.

Next, a liquid containing the specimen 62 is dropped from the specimen dropping means 20 onto the detection surface of the microstructure 80. Then, the liquid (solvent) on the detection surface is dried.

Drying the liquid results in a state as illustrated in FIG. 8B where the specimen 62 is attached to the surfaces of the metallic particles 84 of the microstructure 80.

Next, a liquid containing the metallic particles 64 are dropped from the metallic particle dropping means 22 onto the detection surface of the microstructure 80. Then, the liquid on the detection surface is dried.

Drying the liquid results in a state as illustrated in FIG. 8C where the metallic particles 64 are attached around the metallic particles 84 to which the specimen 62 is attached.

Thus, the inspection chip may be produced also by using the microstructure that has numerous metallic particles 84 secured to the substrate 82.

Further, also the inspection chip produced using the microstructure 80 is capable of trapping the specimen 62 between the metallic particles 64 and the metallic particles 84 forming projections on the surface of the substrate 82. Thus, a further enhanced electric field can be created around the specimen 62, which enhances Raman scattered light produced from the specimen 62. Accordingly, the specimen detecting device produced using the microstructure 80 is also capable a high-sensitivity detection of the specimen.

Figure 9:
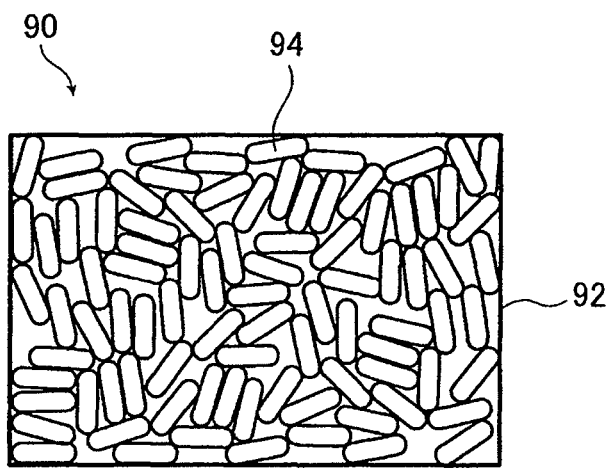
FIG. 9 is a top plan view illustrating a schematic configuration of another example of microstructure.

FIG. 9 is a top plan view illustrating a schematic configuration of another example of the microstructure.

A microstructure 90 illustrated in FIG. 9 comprises a substrate 92 and numerous metallic nanorods 94 disposed on the substrate 92.

The substrate 92 has substantially the same configuration as the substrate 82 described earlier, and therefore detailed description thereof will not be given here.

The metallic nanorods 94 are metallic nanoparticles each having dimensions permitting excitation of localized plasmons and each shaped like a rod having the minor axis and the major axis different in length from each other. The metallic nanorods 94 are secured so that they are fixedly disposed on one surface of the substrate 92. The minor axis of the metallic nanorods 94 measures about 3 nm to 50 nm, and the major axis measures about 25 nm to 1000 nm. The major axis is smaller than the wavelength of the excitation light. The metallic nanorods 94 may be formed of the same metal as the metallic particles described above. For details of the configuration of metallic nanorods, reference may be had, for example, to JP 2007-139612 A.

The microstructure 90 may be produced by the same method as described above for the microstructure 80.

The microstructure 90 having such a configuration also produces localized plasmons around the metallic nanorods and creates an enhanced electric field when the detection surface on which the metallic nanorods are disposed are irradiated by the excitation light.

Thus, also where the microstructure 90 having the above configuration is used, the inspection chip can be likewise produced as when using the microstructure 12 and the microstructure 80 and, furthermore, the specimen can be detected with a high sensitivity.

Figure 10A:
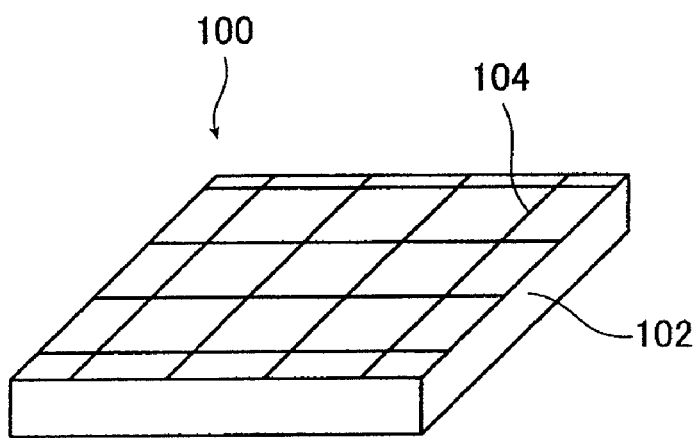
FIG. 10A is a perspective view illustrating a schematic configuration of another example of microstructure.
Figure 10B:
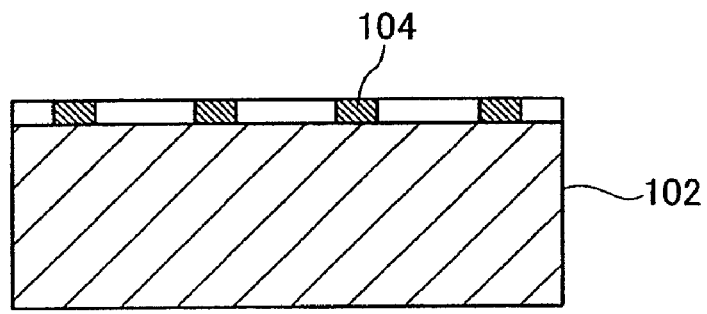
FIG. 10B is a sectional view of FIG. 10A.

Now, reference is made to FIG. 10A, which is a perspective view illustrating a schematic configuration of another example of the microstructure; FIG. 10B is a sectional view of FIG. 10A.

A microstructure 100 illustrated in FIG. 10 comprises a substrate 102 and numerous thin metallic wires 104 provided on the substrate 102.

The substrate 102 has substantially the same configuration as the substrate 82 described earlier, and therefore detailed description thereof will not be given here.

The thin metallic wires 104 are linear members each having a line width permitting excitation of localized plasmons and arranged like a grid on one surface of the substrate 102. The thin metallic wires 104 may be formed of the same metal as the metallic particles and the metallic members described earlier. The thin metallic wires 104 may be produced by any of various methods used to produce metallic wiring including but not limited to vapor deposition and plating.

The line width of the thin metallic wires 104 is preferably not greater than a mean free path of electrons that oscillate in metal in response to light and specifically 50 nm or less, and preferably 30 nm or less. The thin metallic wires 104 may be arranged in any pattern including but not limited to a pattern where the thin metallic wires do not cross each other, i.e., are parallel to each other. The thin metallic wires 104 are also not limited in shape to straight lines and may be curved lines.

The microstructure 100 having such a configuration also produces localized plasmons around the thin metallic wires and creates an enhanced electric field when the detection surface on which the thin metallic wires are arranged is irradiated by the excitation light.

Thus, also when the microstructure 100 having the above configuration is used, the inspection chip can be likewise produced as when using the microstructure 12, the microstructure 80, and the microstructure 90 and, furthermore, the specimen can be detected with a high sensitivity.

Further, the microstructure is not limited to the microstructure 12, the microstructure 80, the microstructure 90, or the microstructure 100; the microstructure may have a configuration comprising projections capable of exciting localized plasmons from each of these microstructures.

Further, where the metallic particles are formed by vapor-deposition on the substrate, the vapor deposition on the substrate may be effected from various directions.

Preferably, the microstructure is so constructed that the metallic particles are first disposed on the substrate, followed by vapor deposition of a metallic film on the substrate to form the projections. Thus, when the metallic film is vapor-deposited after the metallic particles are disposed, the metallic film can be formed between the metallic particles (fine metallic particles) so that the metallic particles and the metallic film can be placed in close contact, and thus the number of hot spots on the detection surface of the microstructure can be increased.

Although the specimen detecting device 10 uses the metallic particle dropping means in order to drop a liquid containing the metallic particles, other methods may be used to dispose or attach the metallic particles onto the detection surface of the microstructure after disposing a specimen on the projections of the detection surface of the microstructure.

Other methods that may be used include, for example, a method whereby a specimen is disposed on the projections on the detection surface of the microstructure, followed by vapor deposition of a metal on the substrate, a method whereby a metallic film is first vapor-deposited on the substrate 82 and then the metallic film is annealed to concentrate the metallic film and produce the metallic particles, and a method whereby a thin film is formed on the substrate 82 and then removed using lithography, etching, sputtering, or like process to leave only the parts thereof that will be metallic particles.

Although the metallic particles are disposed (or attached) after disposing a specimen on the projections of the microstructure in any of the above embodiments, the invention is not limited thereto; a liquid containing both a specimen and the metallic particles may be poured (or dropped) to the microstructure to produce the above inspection chip.

Although the microstructure is dried before irradiating the detection surface with light to detect Raman scattered light of the specimen in any of the above embodiments, the invention is not limited thereto; measurement may be made under conditions where a liquid containing both the specimen and the metallic particles has been only poured to the microstructure, that is, the inspection surface is wet.

Although, in any of the above embodiments, the specific binding substance is not secured to the metallic particles or the projections of the microstructure by surface modification but instead the specimen is trapped between the metallic particles and the microstructure, the invention is not so limited; a specific binding material may be secured to the metallic particles or the projections of the microstructure by surface modification.

When a specific binding material is disposed on either of the metallic particles and the projections of the microstructure, a specific specimen (i.e., a specimen having a disposition to bind to the specific binding material) can be bound to the metallic particles or the projections of the microstructure. Thus, a specific specimen, for example, a specimen to be detected, can be adsorbed onto the metallic particles or the projections of the microstructure. Thus, the specific specimen can be detected with an increased certainty.

Further, the specimen and a specific binding substance can be bound even when the specimen is small because only one specific binding substance is bound to one specimen.

Note that the embodiments of the inspection chip producing method and the specimen detecting method of the invention described above in detail are only illustrative and not restrictive of the invention and that various improvements and modifications may be made without departing from the spirit of the invention.

For example, the specimen detecting device may be provided with drying means for drying the detection surface. The drying means may for example be a heater for heating the detection surface of the microstructure.

When the drying means is provided to dry the detection surface, the liquid component lying on the detection surface can be removed in a shorter period of time, achieving a quick detection of the specimen.

Further, although the specimen detecting device described above detects Raman scattered light of the specimen, the invention is not limited thereto; it may be used in various types of detection devices and detection methods for detecting property values from a specimen that are increased by the creation of an enhanced electric field. For example, the specimen detecting device of the invention may be used for a method whereby nonlinear optical effects (e.g., generation of second harmonic) are increased by an enhanced electric field to detect a specimen and a method whereby a fluorescence from a specimen or a fluorescence from a fluorescent substance having a specimen trapped therein is intensified by an enhanced electric field to achieve detection.

What is claimed is:

1. A method of producing an inspection chip comprising:
    a microstructure producing step of producing a microstructure where metallic portions having dimensions permitting excitation of localized plasmons are formed and distributed on one surface of a substrate;
    a specimen attaching step of attaching a specimen to surfaces of the metallic portions of the microstructure; and
    a metallic particle attaching step of attaching metallic particles having dimensions permitting excitation of surface plasmons to the specimen;
    wherein the specimen is attached to the metallic portions to which no substance capable of specifically binding to the specimen is secured in the specimen attaching step, and/or the metallic particles to which no substance capable of specifically binding to the specimen is secured are attached to the specimen in the metallic particle attaching step.

2. The method of producing an inspection chip according to claim 1, wherein the specimen attaching step and the metallic particle attaching step are performed simultaneously.

3. The method of producing an inspection chip according to claim 1, wherein metallic particles are attached to the substrate to produce the metallic portions in the microstructure producing step.

4. The method of producing an inspection chip according to claim 1, wherein the substrate is anodized, micropores are formed in the one surface of the substrate, thereafter the substrate is plated, and a metal is filled in the micropores until it projects above the one surface of the substrate to form the metallic portions.

5. A method of detecting a specimen comprising:
    an inspection chip producing step of producing an inspection chip using the method of producing an inspection chip according to claim 1;
    a measuring step of irradiating the substrate with light to measure light transmitted through or reflected by a plane in which the metallic portions are formed; and
    a detecting step of detecting the specimen based upon intensity of light measured in the measuring step.

6. The method of detecting a specimen according to claim 5, wherein measurement is made in the measuring step when the substrate has a liquid thereon.

7. The method of detecting a specimen according to claim 5, wherein measurement is made in the measuring step when the one surface of the substrate is dry.

8. The method of producing an inspection chip according to claim 1, wherein the metallic particle attaching step is performed by dropping a given amount of liquid containing the metallic particles onto the detection surface of the microstructure.

9. A method of producing an inspection chip comprising:
a microstructure producing step of producing a microstructure where metallic portions having dimensions permitting excitation of localized plasmons are formed and distributed on one surface of a substrate;
a specimen attaching step of attaching a specimen to surfaces of the metallic portions of the microstructure; and
a metallic particle attaching step of attaching metallic particles having dimensions permitting excitation of surface plasmons to the specimen,
wherein the steps are performed in the above-recited order, and
wherein at least one of the following occurs:
the specimen is attached to the metallic portions to which no substance capable of specifically binding to the specimen is secured in the specimen attaching step, and
the metallic particles to which no substance capable of specifically binding to the specimen is secured are attached to the specimen in the metallic particle attaching step.

10. The method of producing an inspection chip according to claim 9, wherein the specimen attaching step and the metallic particle attaching step are performed simultaneously.

11. The method of producing an inspection chip according to claim 9, wherein metallic particles are attached to the substrate to produce the metallic portions in the microstructure producing step.

12. The method of producing an inspection chip according to claim 9, wherein the substrate is anodized, micropores are formed in the one surface of the substrate, thereafter the substrate is plated, and a metal is filled in the micropores until it projects above the one surface of the substrate to form the metallic portions.

13. The method of producing an inspection chip according to claim 9, wherein the metallic particle attaching step is performed by dropping a given amount of liquid containing the metallic particles onto the detection surface of the microstructure.

14. A method of producing an inspection chip comprising:
a microstructure producing step of producing a microstructure where metallic portions having dimensions permitting excitation of localized plasmons are formed and distributed on one surface of a substrate;
a specimen attaching step of attaching a specimen to surfaces of the metallic portions of the microstructure; and
a metallic particle attaching step of attaching metallic particles having dimensions permitting excitation of surface plasmons to the specimen in this order,
wherein the steps are performed in the above-recited order, and
wherein the specimen is attached to the metallic portions to which no substance capable of specifically binding to the specimen is secured in the specimen attaching step, and the metallic particles to which no substance capable of specifically binding to the specimen is secured are attached to the specimen in the metallic particle attaching step.

15. The method of producing an inspection chip according to claim 14, wherein the specimen attaching step and the metallic particle attaching step are performed simultaneously.

16. The method of producing an inspection chip according to claim 14, wherein metallic particles are attached to the substrate to produce the metallic portions in the microstructure producing step.

17. The method of producing an inspection chip according to claim 14, wherein the substrate is anodized, micropores are formed in the one surface of the substrate, thereafter the substrate is plated, and a metal is filled in the micropores until it projects above the one surface of the substrate to form the metallic portions.

18. The method of producing an inspection chip according to claim 14, wherein the metallic particle attaching step is performed by dropping a given amount of liquid containing the metallic particles onto the detection surface of the microstructure.

* * * * *

UNITED STATES PATENT AND TRADEMARK OFFICE
CERTIFICATE OF CORRECTION

PATENT NO. : 8,045,171 B2  
APPLICATION NO. : 12/390905  
DATED : October 25, 2011  
INVENTOR(S) : Naoki Murakami and Yuichi Tomaru Page 1 of 1

It is certified that error appears in the above-identified patent and that said Letters Patent is hereby corrected as shown below:

On the title page, it should read:

Item --(73) Assignee: FUJIFILM Corporation, Tokyo (JP)--

Signed and Sealed this
Fourteenth Day of February, 2012

David J. Kappos
*Director of the United States Patent and Trademark Office*